US012017560B2

(12) United States Patent
Wu

(10) Patent No.: US 12,017,560 B2
(45) Date of Patent: Jun. 25, 2024

(54) PREDICTIVE CONTROL SYSTEM FOR A VEHICLE

(71) Applicant: SZ DJI TECHNOLOGY CO., LTD., Shenzhen (CN)

(72) Inventor: Jun Wu, Shenzhen (CN)

(73) Assignee: SZ DJI TECHNOLOGY CO., LTD., Shenzhen (CN)

( * ) Notice: Subject to any disclaimer, the term of this patent is extended or adjusted under 35 U.S.C. 154(b) by 583 days.

(21) Appl. No.: 17/139,802

(22) Filed: Dec. 31, 2020

(65) Prior Publication Data

US 2021/0146803 A1 May 20, 2021

Related U.S. Application Data

(63) Continuation of application No. PCT/CN2019/100369, filed on Aug. 13, 2019.

(51) Int. Cl.
*B60N 2/02* (2006.01)
*B60N 2/00* (2006.01)
(Continued)

(52) U.S. Cl.
CPC .......... *B60N 2/0296* (2013.01); *B60N 2/002* (2013.01); *B60N 2/02246* (2023.08); *B60W 40/04* (2013.01); *B60W 40/06* (2013.01); *B60W 40/08* (2013.01); *B60W 50/0097* (2013.01); *B60W 50/14* (2013.01); *B60W 60/001* (2020.02);
(Continued)

(58) Field of Classification Search
CPC .. B60N 2/0296; B60N 2/02246; B60N 2/002; B60W 60/001; B60W 40/04; B60W 40/06; B60W 40/08; B60W 50/0097; B60W 50/14; B60W 2556/10; B60W 2555/20; B60W 2540/221; B60W 2050/146; B60W 2420/40; B60W 2420/52; B60W 2420/54;
(Continued)

(56) References Cited

U.S. PATENT DOCUMENTS

2018/0118054 A1    5/2018  Devilbiss et al.
2019/0196481 A1*   6/2019  Tay .......................... G01S 17/86
(Continued)

FOREIGN PATENT DOCUMENTS

CN         106114111 A       11/2016
CN         106828207 A       6/2017
(Continued)

OTHER PUBLICATIONS

International Search Report from the National Intellectual Property Administration for International Application No. PCT/CN2019/100369, dated Apr. 26, 2020 (10 pages).

*Primary Examiner* — Behrang Badii
*Assistant Examiner* — Jay Khandpur
(74) *Attorney, Agent, or Firm* — XSENSUS LLP

(57) ABSTRACT

Apparatuses, systems and methods to ameliorate adverse effects upon the occupant based on predicted movements are provided. Predictions to movements of the vehicle can be accomplished by detecting operations of one or more velocity control mechanisms, and/or using various types of sensors. One or more processors can be used to derive the predicted movements, and to issue actuation signals to actuators to alter operations of the vehicle and/or a seat or other controlled devices with which the occupant interacts within the vehicle.

20 Claims, 7 Drawing Sheets

(51) Int. Cl.
  *B60W 40/04* (2006.01)
  *B60W 40/06* (2012.01)
  *B60W 40/08* (2012.01)
  *B60W 50/00* (2006.01)
  *B60W 50/14* (2020.01)
  *B60W 60/00* (2020.01)

(52) U.S. Cl.
  CPC ... *B60W 2050/146* (2013.01); *B60W 2420/40* (2013.01); *B60W 2420/408* (2024.01); *B60W 2420/54* (2013.01); *B60W 2540/10* (2013.01); *B60W 2540/12* (2013.01); *B60W 2540/14* (2013.01); *B60W 2540/221* (2020.02); *B60W 2555/20* (2020.02); *B60W 2556/10* (2020.02)

(58) Field of Classification Search
  CPC ......... B60W 2540/10; B60W 2540/12; B60W 2540/14
  See application file for complete search history.

(56) References Cited

U.S. PATENT DOCUMENTS

| | | | |
|---|---|---|---|
| 2020/0057453 A1* | 2/2020 | Laws | G08G 1/22 |
| 2020/0079385 A1* | 3/2020 | Beaurepaire | B60W 30/025 |
| 2020/0238953 A1* | 7/2020 | Spasovski | G06V 20/59 |
| 2020/0298732 A1* | 9/2020 | Gandhi | B60N 2/0224 |
| 2021/0221258 A1* | 7/2021 | Ekchian | B60N 2/995 |
| 2021/0221264 A1* | 7/2021 | Selden | B60N 2/502 |
| 2021/0355740 A1* | 11/2021 | Hwang | B60N 3/104 |

FOREIGN PATENT DOCUMENTS

| | | |
|---|---|---|
| CN | 107662569 A | 2/2018 |
| CN | 107696921 A | 2/2018 |
| CN | 107933495 A | 4/2018 |
| CN | 108372849 A | 8/2018 |
| DE | 4201412 A1 | 7/1993 |
| DE | 102015015306 A1 | 5/2016 |
| JP | 2001-071803 A | 3/2001 |
| JP | 2006-341637 A | 12/2006 |
| JP | 2008-097058 A | 4/2008 |
| JP | 2017-137023 A | 8/2017 |
| KR | 2006-0102018 A | 9/2006 |

\* cited by examiner

PREDICTIVE CONTROL SYSTEM FOR A VEHICLE

CROSS-REFERENCE TO RELATED PATENT APPLICATIONS

This application is a continuation of International Application No. PCT/CN2019/100369, filed Aug. 13, 2019, which is hereby incorporated by reference in its entirety.

FIELD OF THE INVENTION

The field of the invention is automobile and other vehicle controls.

BACKGROUND

The following description includes information that may be useful in understanding the present invention.

Whether traveling by vehicles for personal usage or for public transportation, occupants (e.g., a driver, a pilot, a rider, a passenger, a pet, goods or cargo, etc.) of those vehicles are sometimes subject to adverse vehicle environments occasioned by undesirable or abrupt movements of the vehicles. The vehicles herein may include various vehicle types (e.g., motor vehicles, trucks, automobiles, motorcycles, bikes, ships, cruises, planes, trains, subways), or any other transportation methods. Undesirable movements include rapid acceleration and deceleration, bumps, turns, vibrations, and so forth that create adverse effects on those various types of vehicles. Adverse effects on occupants of the vehicles can range anywhere from minor annoyance to major physiological or psychological discomfort.

Existing systems provide resolutions by modulating undesirable vehicle motions. For example, it is known for automobiles to use suspension components, such as shock absorbers including various springs or hydraulic pistons, to ameliorate bumps and vibrations. However, any given suspension component is not necessarily appropriate for all adverse conditions. For example, in circumstances where excessive suspension movements occurred due to extremely rough road conditions, the result of applying shock absorbers to damp spring oscillations may be limited by the mechanical structures of the suspension components. Some vehicles have adjustable suspensions, which can be actuated by an occupant, while some vehicles have adjustable suspensions that can be actuated automatically, for example, the adjustable suspensions can be actuated automatically when the vehicle is making turns. However, adjustable suspension systems, actuated manually or automatically, have the similar problem described above that are caused by the structural limitations of suspension components, and thus, are not appropriate to absorb and dissipate all excessive energy from springs for all adverse conditions.

One issue remains unaddressed in the known systems is the systems are designed to be reactive rather than predictive. More specifically, the adjustable or non-adjustable suspension systems are both designed to react after the undesirable movements come into effects on the vehicles, such as absorbing excessive energy from the springs to damp spring oscillations after a bump or a severe vibration has occurred. This issue can be particularly important where a desired alteration of suspensions to the vehicle requires several seconds or more reaction time to implement. Carrying on with the example above, an automobile might come up upon several meters of rough road surface, and by the time a change to the suspensions implemented, the automobile has already driven past the rough road surface. Similarly, if a driver pushes down hard on a gas pedal, there is frequently a lag of a few seconds before there is a significant acceleration. If the vehicle waits for the acceleration to occur before adjusting suspensions of the vehicle, it may be too late to properly accommodate the driver occupying a seat of the vehicle.

Thus, there is still a need for apparatuses, systems and methods that predict movements of a vehicle in advance, and proactively alter a vehicle environment of an occupant of the vehicle in a manner designed to ameliorate or compensate adverse effects on the occupant caused by the predicted movements.

SUMMARY OF THE INVENTION

The inventive subject matter provides apparatuses, systems and methods in which movements of a vehicle are predicted and used to proactively alter a vehicle environment of an occupant for ameliorating adverse effects upon the occupant caused by the predicted movements.

Examples of the present disclosure provide predictions to movements of the vehicle and proactive alterations to a vehicle environment for improving onboard experiences of an occupant of the vehicle. Predictions to movements of the vehicle can be accomplished in any suitable manner, including by detecting operations of a velocity control mechanism. In various embodiments of the present disclosure, the velocity control mechanism may include mechanical control mechanisms and/or electrical control mechanisms. For example, the mechanical control mechanisms may be associated with the operations of a gas pedal, a brake pedal, and/or a steering wheel. The electrical control mechanisms may be associated with a drive-by-wire (i.e., drive by wire, steer-by-wire, fly-by wire, or x-by-wire) system that utilizes electrical or electro-mechanical systems to perform vehicle functions that are traditionally operated by mechanical linkages. In various embodiments, operations of a gas pedal, a brake, a steering wheel, and/or a drive-by-wheel system (or other velocity control mechanisms) generate signals used to predict future movements of the vehicle. Based on the prediction, the system can use actuators to proactively alter the position or orientation of the seat of an occupant for ameliorating adverse effects on the occupant that might otherwise occur.

It is contemplated that the velocity control mechanism(s) can be operated from within the vehicle, from outside the vehicle, or a combination of both. Predictions to movements of the vehicle can also be obtained using inputs from one or more sensors, such as active sensors or passive sensors (i.e., sensors that are not actively operated by an occupant or other agents). In various embodiments of the present disclosure, example sensors include a pressure sensor, a motion sensor (e.g., an inertial measurement unit (IMU)), a light detection and ranging (LIDAR) sensor, a light sensor (an infrared sensor, an ultraviolet sensor, a laser sensor, etc.), a camera, a location sensor (e.g., a global positioning system (GPS) receiver), a sound sensor (an ultrasound sensor, etc.), and so forth. Some of these sensors can be used to predict movements of the vehicle based upon a change in an upcoming road condition, upcoming traffic or ambient weather. Based on such predictions, the vehicle environment of an occupant of the vehicle can be altered, for example, by engaging a four-wheel drive (4WD) or other anti-slip technology, or by slowing down the speed of the vehicle.

Any one or more of such sensors mentioned above can be located in or on the vehicle (refers to the onboard sensors hereinafter), or distal from the vehicle (refers to the off-board sensors hereinafter).

In various embodiments of the present disclosure, a processor is used to derive predicted movements from one or more sensors, and to transmit actuation signals to one or more actuators. In some embodiments, the processor can be programmed to produce an actuation signal that is at least partially based on a past actuation signal derived from a historical experience regarding historical movements that are similar to the current predicted movements. In other embodiments, actuation signals can also be produced by taking into account a characteristic of an occupant of the vehicle. In such embodiments, the characteristic of the occupant may include one or more information related to a weight, a height, a spinal curvature, a flexibility, a body temperature, a sitting height, a shoulder width, a hip width, a waist width, a chest size, an age, a gender, a physical disability, a health condition, or a mental condition of the occupant. For example, where rough road is anticipated, it might be appropriate to alter configurations of the shocks of a vehicle to one degree for a lightweight occupant and to alter configurations of the shocks to another degree for a heavier occupant.

In various embodiments of the present disclosure, example alterations to the vehicle environment include seat, steering wheel, or other physical adjustments, music or other auditory adjustments, and/or display or other visual adjustments. For example, seat adjustments in the present disclosure may include adjusting at least one of a distance, an orientation, a disposition, an inclination, a height, a temperature, or a rigidity of any one or more components of the seat. Other example alterations to the vehicle environment include modifying at least one of a spatial position, aa tension of a seat restraint or a seat belt, or the suspension system of the vehicle.

All manner of vehicles is contemplated, whether the vehicles are used to travel by land, sea, air or a combination of those modes. In various embodiments of the present disclosure, example vehicles include occupant-driven or self-driving vehicles, drones, or other non-occupant-driven vehicles. Example vehicles also include vehicles used for specific purposes, including vehicles for private, public, governmental, or military usages.

Various embodiments of the present disclosure resolve a significant technical problem of how to proactively accommodate vehicle movements that can produce undesirable effects on an occupant of the vehicle. A processor, coupled to various sensors and/or control units, is provided to predict potentially adverse movements. The processor is further provided to make predictive adjustments to the occupant's seat, other aspects of the vehicle, or the vehicle environment for ameliorating an adverse effect that is likely to occur based on the predictive movements.

Various objects, features, aspects and advantages of the inventive subject matter will become more apparent from the following detailed description of preferred embodiments, along with the accompanying drawing figures in which like numerals represent like components.

DETAILED DESCRIPTION

Figure 1:
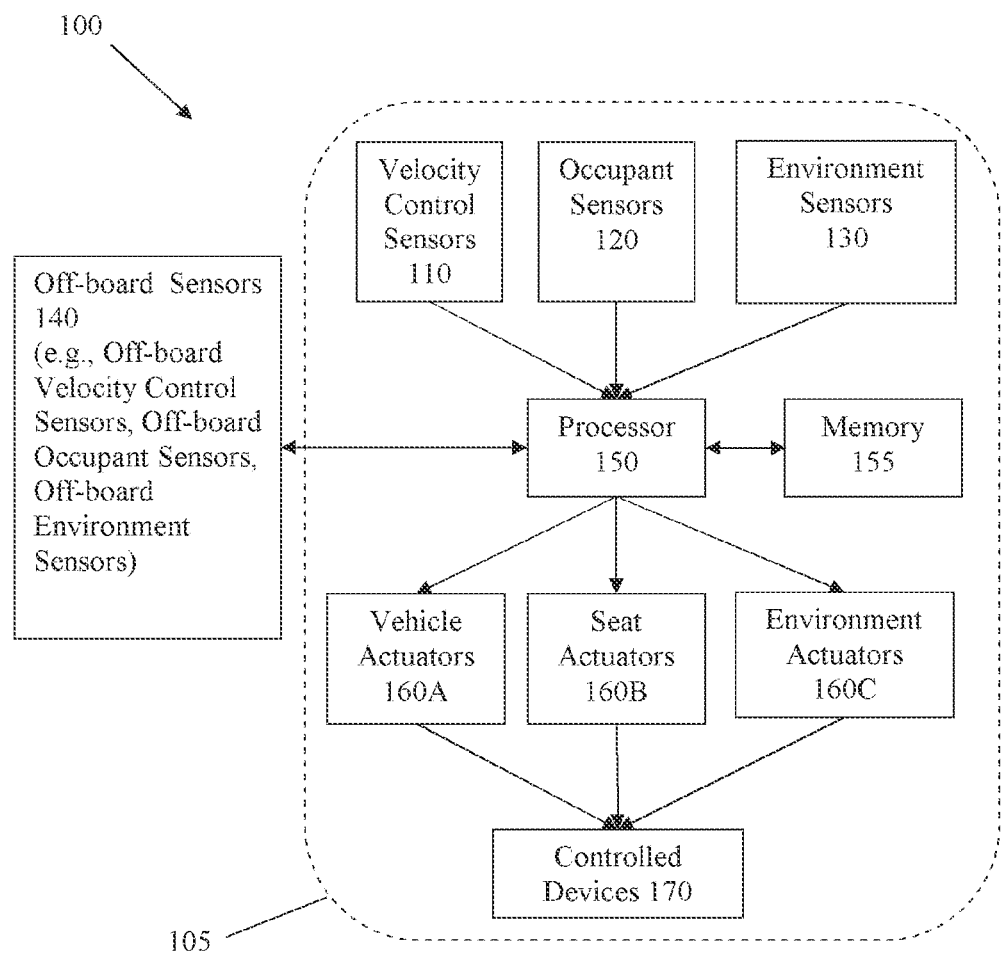
FIG. 1 is an example schematic of a predictive control system of a vehicle configured to proactively ameliorate or compensate adverse effects on an occupant based on predicting movements of the vehicle.

Throughout the following discussion, numerous references will be made regarding processors, servers, services, interfaces, portals, platforms, or other systems formed from computing devices. It should be appreciated that the use of such terms is deemed to represent one or more computing devices having at least one processor configured to execute software instructions stored on a computer readable tangible, non-transitory medium. For example, as used herein a "processor" can include any of a cloud computing service, one or more separate computers, and/or one or more processing chips or cores, operating in any manner to fulfill the herein described roles, responsibilities, or functions.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g. "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

The following discussion provides many example embodiments of the inventive subject matter. Although each embodiment represents a single combination of inventive elements, the inventive subject matter is considered to include all possible combinations of the disclosed elements. Thus if one embodiment comprises elements A, B, and C, and a second embodiment comprises elements B and D, then the inventive subject matter is also considered to include other remaining combinations of A, B, C, or D, even if not explicitly disclosed.

As used herein, and unless the context dictates otherwise, the term "coupled to" is intended to include both direct coupling (in which two elements that are coupled to each other contact each other) and indirect coupling (in which at least one additional element is located between the two elements that are coupled to each other). Therefore, the terms "coupled to" and "coupled with" are used synonymously.

FIG. 1 is an example schematic of a predictive control system 100 of a vehicle 105 configured to proactively ameliorate or compensate adverse effects on an occupant based on predicting movements of the vehicle 105.

In FIG. 1, a predictive control system 100 generally includes various onboard sensors 110, 120, and/or 130 and various off-board sensors 140 (such as off-board velocity control sensors, off-board occupant sensors, and/or off-board environment sensors) that provide information to a processor 150. The processor 150 in turn uses the provided information to operate various actuators 160A, 160B, 160C to control the controlled devices 170 that affect the occupant. Of particular significance in this application is that the processor 150 is programmed to use information derived from the sensors 110, 120, 130, and/or 140 to predict accelerations, jerks, bumps or other movements of the vehicle 105, and to use that predicted movements to operate controls to at least partially ameliorate or compensate an adverse effect on the occupant caused by the predicted movements.

The broken line indicates schematically that some of these components (e.g., sensors 110, 120, 130) are onboard sensors, i.e., sensors that are physically located at least partially in or on a vehicle 105. Other components (e.g., sensors 140) are off-board sensors, and only informationally coupled to the vehicle 105. The off-board sensors 140 may include off-board velocity control sensors, off-board occupant sensors, or off-board environment sensors. In embodiments, sensors that detect operations of a gas pedal or a brake pedal by an occupant in a fuel-powered automobile fall within the category of onboard velocity control sensors 110, while sensors detecting operations of a joystick of a vehicle by a distant pilot fall within the category of off-board sensors 140.

FIG. 1 is intentionally shown as a schematic, to include within the scope any sort of vehicles that has a seat, a bed or other components configured to hold an occupant in a seated position, a lying position, or other positions that can be actively modified under control of the processor 150. Examples of the vehicle 105 include automobiles, buses, trucks, trains, cable cars, trolleys, amusement park rides, ships, boats, and/or aircrafts. Vehicle 105 should also be interpreted broadly to include vehicles that are occupant-driven vehicles, vehicles operated from external control personnel, and/or self-driving vehicles. For example, one embodiment of the vehicle 105 is an aircraft drone having a passenger seat or cot configured to extract a soldier from a combat zone. Another example of vehicle 105 is a self-driving lorry used to transport goods from one city to another, which also has a seat for a driver who can operate the lorry in difficult traffic. Still another example of vehicle 105 is a self-driving automobile or bus, configured to transport passengers in seats, without requiring any of the passengers to drive the vehicle.

As used herein, the term "occupant" preferably refers to a human, a driver, a pilot, a rider, or a passenger, but can also refer to a house pet (e.g., a dog or a cat), a farm animal (e.g., a pig, a horse or a cow), other animals, goods, or cargo. For example, an occupant may be a driver operating a vehicle or a passenger occupying a seat of the vehicle. In such an example, the proposed active seat control system may predict the movements of the vehicle for proactively adjusting the vehicle environment (such as adjusting the orientation, inclination, tilting angle, or rigidity of the seat) to ameliorate, eliminate, offset or compensate an adverse effect that would likely occur due to the predicted movements. For another example, an occupant may be an animal or a pet to be shipped to a farm or a zoo. The animal or the pet may occupy an adjustable seat or a movable tray/cage of a truck, a train, or an aircraft for transporting the animal or the pet. In such an example, the proposed active seat control system may predict future movements of the truck for proactively altering the truck environment (such as adjusting the position, orientation, or inclination of the adjustable seat or the movable tray/cage) to hold the animal or the pet in a stable position and to prevent adverse emotions (e.g., anger, anxiety, fear, etc.) or discomforts of the animal or pet that would likely occur due to the adverse vehicle environment caused by upcoming adverse transporting conditions. For another example, an occupant may be fragile goods to be shipped from a merchant/vendor to a consumer/customer occupying a seat of a vehicle or a delivery truck for goods shipment. In such an example, the proposed active seat control system may predict future movements of the truck based on detected upcoming road conditions, delivery routes or map data, etc. The predicted future movements may be used to proactively alter the vehicle environment, such as tightening cargo ropes, to prevent damages to fragile goods that would likely occur due to excessive jerky movements or vibrations caused by upcoming adverse road conditions. For another example, an occupant may be products to be transported from one location to another within an indoor environment, such as a warehouse or a retailer store, to be stored separately based on different categories of the products. The products may occupy a storage structure of a self-driving vehicle for dispatching different categories of products to different, designated areas within the warehouse. In such an example, the proposed active seat control system may predict future movements of the self-driving vehicle based on information associated with the indoor layout of warehouse or dispatching routes for categorizing different products, etc., to prevent adverse situations, such as products being damages or fallen out of the self-driving vehicle, to occur. References herein refer to "an" or "the" occupant should be read as contemplating that the vehicle might or might not have other occupants.

Figure 2:
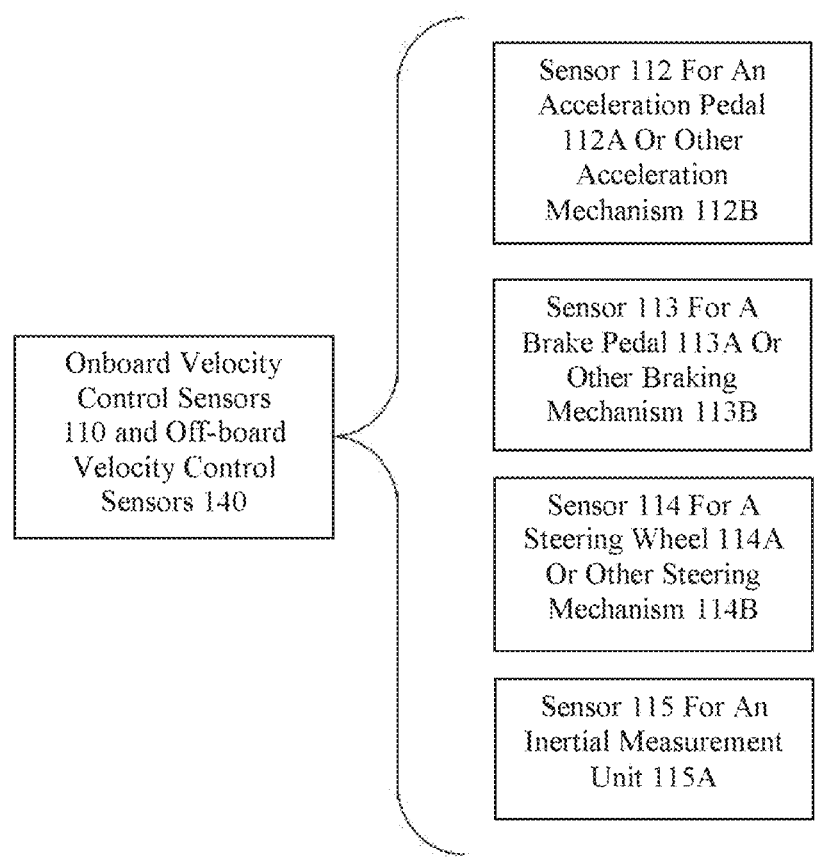
FIG. 2 is a graphic identifying various example onboard velocity control sensors and off-board velocity control sensors.

FIG. 2 illustrates various example onboard velocity control sensors 110 and off-board velocity control sensors 140.

As shown in FIG. 2, onboard velocity control sensors 110 should be interpreted herein to mean any device that is located at least partially within or on the vehicle for detecting operations related to a velocity control of the vehicle. In some embodiments, the onboard velocity control sensors 110 may include, for example, a sensor 112 that detects operations associated with a gas pedal, an acceleration pedal, other acceleration foot pedals 112A or other acceleration mechanisms 112B. In such embodiments, the processor 150 may receive control signals generated based on the operations detected by the sensor 112 (e.g., an acceleration pedal) and predict an accelerating movement of the vehicle.

In embodiments, the calculation/determination of the prediction may not only use currently received control signals obtained from sensor detections, but may also use historical control signals retrieved by the processor 150 from a memory 155 storing historical detected sensor data and historical control signals. Specifically, historical control signal may be associated with an occupant profile, such as a driver profile. In such an example, the driver profile may record historical control signals that are associated with a driver's driving habits, commuting routes and time, posture or sitting habits, etc. The currently detected control signals and historical control signals may be jointly utilized or be blended, by way of using signal mixing or blending techniques (such as a sensor fusion process), to provide a more accurate prediction result.

For example, the historical control signals may include information regarding the driver's driving habits, such as an average rotation angle the driver is likely to use when making turns. Based on the average rotation angle, the proposed active seat control system may provide more accurate predictions for calculating a corresponding rotation angle of the seat to offset/compensate the average rotation angle predicted based on the driver's driving habit while turning movements are likely to occur.

For another example, the historical control signals may further include information regarding the driver's commuting routes and time. The historical control signals may include information including a commuting route from the driver's residence to the work place. The historical control signals may further incorporate other traffic information detected from onboard or off-board velocity control sensors 110, 140 that is stored within the memory, such as locations of traffic lights, stop signs, or an estimated departure/arrival time associated with the commuting route and the driver. In such an example, the proposed active seat control system may utilize information of the commuting route to predict where the vehicle would likely to go straight, make left turns, or make right turns, and utilize other information to determine when the vehicle would likely to accelerate and decelerate, such as predicting a decelerate when approaching the locations of the traffic lights or stop signs on the route, for providing a better prediction of the movements of the vehicles. In embodiments, the historical control signals may further incorporate yet additional traffic information based on the time of the date, such as a daytime or a night time, or the seasons of the year, such as a long weekend or a holiday season. For example, during the daytime or long weekend, the vehicle is likely to be operated in a slower speed than during the night time or regular weekend because of the heavier traffic. In such an example, a deceleration movement may likely to be predicted due to the heavy traffic and multiple stops/pauses.

For another example, the historical control signals may further include information regarding a driver's posture or sitting habit. The historical control signals may include information, such as a sitting height, an inclination angle, or a rigidity that records a specific driver or a passenger's preferences. In such an example, the proposed active seat control system may be customized to adjust the vehicle environment while holding the driver or the passenger on the seats. In embodiments, the proposed active seat control system may incorporate the currently detected velocity control signals and historical signals regarding a driver or passenger's posture or sitting habit to alter the seat height (such as increasing the seat height when an upcoming cavity is detected or decreasing the seat height when an upcoming bump is detected), the orientation (such as turning the seat when a curved road or turning movements are detected), the rigidity (such as decreasing the rigidity level of the seat when a vibration is detected due to uneven payment of the road), or the inclination angle of the seat (such as inclining the seat backward for deceleration in circumstances where a red light or a stop sign is detected), for providing a better prediction of movements of the vehicles and actuating corresponding compensating adjustments to the seat.

It is should be understood that the prediction of the acceleration of the vehicle may be based on one or more of currently detected control signals generated by a sensor 112 that detects operations associated with a gas pedal, an acceleration pedal, other acceleration foot pedals 112A or other acceleration mechanisms 112B, as well as historical control signals associated with similar acceleration movements, or a combination of both currently detected and historical control signals. Specifically, the prediction of the acceleration of the vehicle may be calculated, by way of using a sensor fusion process, based on currently detected control signals and/or historical control signals derived from similar acceleration operations detected by the sensor 112 (e.g., an acceleration pedal) in history to provide a more accurate prediction result. The historical control signals may be stored in the memory 155 and are retrievable whenever similar acceleration operations are detected.

In other embodiments, the onboard velocity control sensors 110 may include a sensor 113 that detects operations associated with a brake pedal 113A or other braking mechanisms 113B. In such embodiments, the processor 150 may receive control signals generated based on the operations detected by the sensor 113 (e.g., a brake pedal) and predict a decelerating movement of the vehicle. The prediction of the deceleration of the vehicle may further be calculated, by way of using a sensor fusion process, based on currently detected control signals and/or historical control signals derived from similar deceleration operations detected by the sensor 113 (e.g., a brake pedal) in history to provide a more accurate prediction result. The historical control signals may be stored in the memory 155 and are retrievable whenever similar deceleration operations are detected.

In other embodiments, the onboard velocity control sensors 110 may include a sensor 114 that detects operation associated with a steering wheel 114A or other steering mechanisms 114B. In such embodiments, the processor 150 may receive control signals generated based on the operations detected by the sensor 114 (e.g., a steering wheel) and predict a turning movement (e.g., making a right turn, a left turn, or a U-turn) of the vehicle. The prediction of the turns of the vehicle may further be calculated, by way of using a sensor fusion process, based on currently detected control signals and/or historical control signals derived from similar turning operations detected by the sensor 114 (e.g., a steering wheel) in history to provide a more accurate prediction result. The historical control signals may be stored in the memory 155 and are retrievable whenever similar turning operations are detected.

In other embodiments, the onboard velocity control sensors 110 may include a sensor 115 that detects operations associated with an IMU 115A. In such embodiments, the processor 150 may receive control signals generated based on the operations detected by the sensor 115 (e.g., an IMU) and predict a movement in three-dimensional (3D) dynamics of the vehicle (e.g., a vibration movement, a rotation movement, a tilting movement, etc.). The prediction of the movements in 3D dynamics of the vehicle may further be calculated, by way of using a sensor fusion process, based on currently detected control signals and/or historical control signals derived from similar operations in 3D dynamics detected by the sensor 115 (e.g., an IMU) in history. The historical control signals may be stored in the memory 155 and are retrievable whenever similar operations in 3D dynamics are detected.

In various embodiments of the present disclosure, the processor 150 may further receive additional control signals from off-board sensors 140. The processor 150 may utilize the received control signals from any one of an onboard sensor, an off-board sensor, or a combination thereof to predict future movements of the vehicle. Embodiments of the example control signals received from the off-board velocity control sensors 140 may include signals related to map data received from off-board sensors coupled to a remote map database storing various map data, GPS signals received from off-board sensors coupled to a remote GPS database storing various latitude and longitude coordinates, control signals received from remote devices (e.g., sensors located on traffic light poles), or other control signals emitted from sensors embedded on other vehicles in the vicinity.

For example, the processor 150 may receive signals related to map data from an off-board sensor coupled to a remote map database. In such an example, the received signals may be used to predict movements of the vehicle based on the relationship between the vehicle and the surrounding areas associated with the map. In circumstances where the vehicle position shows that the vehicle is approaching a crossroad or and intersection based on the map data, a future deceleration, turning, or acceleration movement may be predicted because the vehicle is likely to slow down for making turns and accelerate at the crossroad or the intersection. For another example, the processor 150 may receive signals from an off-board sensor coupled to a remote GPS database comprising various GPS coordinates. In such an example, the received signals may be used to predict movements of vehicle based on the received GPS coordinates associated with the vehicle's geographic locations. In circumstances where the GPS coordinates surrounding the vehicle's GPS coordinates show that the vehicle is approaching an area with increasing or decreasing altitude/elevation changes, a future deceleration or acceleration may be predicted because the vehicle is likely to slow down on an upward slope road section and speed up on a downward slope road section.

For another example, the processor 150 may receive control signals from remote devices embedded on a fixed object, such as a traffic light pole or a road sign. In such an example, the received signals may be used to predict movements of the vehicle based on a traffic condition or a distance between the vehicle and the traffic light pole or the road sign or between the vehicle and other vehicles. In circumstances where the processor 150 receives control signals from a range sensor (such as a LIDAR or any kind of light sensor, a camera or any kind of image sensor, or any kind of sound sensor, etc.) located on the traffic light pole or the road sign (such as a stop sign), a future deceleration and stop movement may be predicted when the range sensor detected a decreasing of distance between the vehicle and the traffic light pole or the road sign because the vehicle is likely to slow down and make a stop at the location of the traffic light pole or the road sign (such as a stop sign).

For another example, the processor 150 may receive control signals emitted from sensors embedded on other vehicles in the vicinity. In embodiments, the processor 150 may receive control signals emitted from sensors embedded on the previous vehicle located in front of the current vehicle the occupant is operating. In such an embodiment, the sensors embedded on the previous vehicle may include various types of range sensors, including a LIDAR sensor or other light sensors (such as a visible light sensor, an infrared sensor, an ultraviolet sensor, a laser sensor, etc.), an ultrasound sensor or other sound sensors, a GPS receiver or other location determining sensors, vision sensors or other image detecting sensors (such as cameras), and/or any kind of distance or proximity sensors, etc. Those sensors may, for example, emit control signals to the current vehicle when the distance between the previous vehicle and current vehicle is smaller than a threshold. In such an example, the processor 150 may predict a deceleration or stop movement because the current vehicle is likely to slow down or stop to avoid colliding into the previous vehicle.

Corresponding off-board velocity control sensors 140 could additionally or alternatively be operated by a person, a computer, a computing entity, or other operational entities external to the vehicle. In embodiments, the processor 150 may receive control signals from the off-board sensors 140 that are generated based on the operations detected by the off-board sensors 140 operated by humans, computers, and/or non-humans. The processor 150 may predict a movement of the vehicle based on the control signals received from the off-board sensors 140. The prediction of the movements of the vehicle may be generated based on the detected control signals and/or historical control signals derived from similar operations detected by the off-board sensors 140 in history. The historical control signals may be stored in the memory 155 and are retrievable whenever similar operations detected by the off-board sensors are transmitted to the processor 150.

In some embodiments, the onboard velocity control sensors 110 or the off-board velocity control sensors 140 described above may further encompass electrical control mechanisms that are associated with a drive-by-wire (i.e., drive by wire, steer-by-wire, fly-by wire, or x-by-wire) system that utilizes electrical or electro-mechanical systems to perform vehicle functions or movements that are traditionally operated by mechanical linkages. In embodiments, the electrical control mechanisms may use onboard or off-board electromechanical actuators and human-machine interfaces, including for example, pedal and steering feel emulators. In such embodiments, the onboard velocity control sensors 110 or the off-board velocity control sensors 140 may be used to predict future movements of the vehicle by detecting electronic signals or electromagnetic signals associated with the drive-by-wire system.

Figure 3:
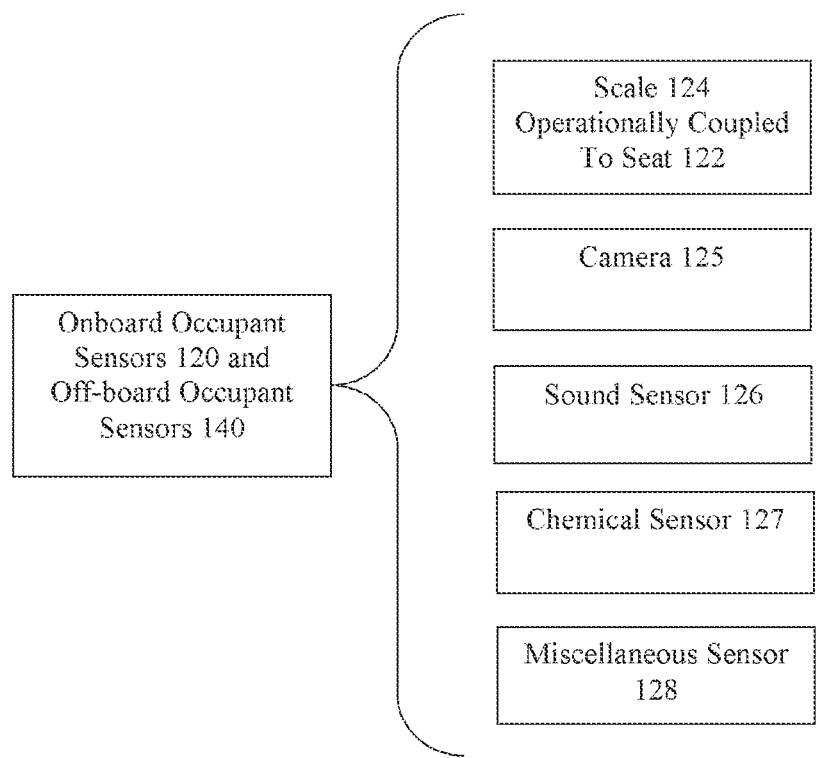
FIG. 3 is a graphic identifying various example onboard occupant sensors and off-board occupant sensors.

FIG. 3 is a graphic identifying various example onboard occupant sensors 120 and off-board occupant sensors 140.

As shown in FIG. 3, onboard occupant sensors 120 may be optionally included in the predictive control system 100 to provide additional control signals to the processor 150. In embodiments, the onboard occupant sensors 120 may generate the additional control signals in response to the detection of a characteristic of the occupant. In embodiments, example characteristics of an occupant that can be sensed include a weight, a height, a spinal curvature, a flexibility, a body temperature, a sitting height, a shoulder width, a hip width, a waist width, a chest size, an age, a gender, a physical disability, a health condition, a mental condition, and/or other biometric features of the occupant. In embodiments, the onboard occupant sensors 120 may include a scale 124 that is operationally coupled to the seat 122 to measure the weight of the occupant, a camera 125 that can measure dimensions of the occupant, a sound sensor 126 that can detect the quality of the occupant's voice or audio instructions from the occupant, or identify the occupant's identity via a voice recognition technique, a chemical sensor 127 that can detect pheromones or other chemical materials being emitted from the occupant, and/or a miscellaneous sensor 128 such as a sensor configured to detect a stretching or other self-controlled motion of the occupant. Optionally, the characteristics of an occupant may also be sensed by off-board occupant sensors located outside of the vehicle 105. The off-board occupant sensors may perform similar functions for detecting characteristics of the occupant and provide additional control signals that are coupled to the processor 150.

In embodiments, the processor 150 may receive the additional control signals generated based on the operations detected by the onboard occupant sensors 120 and/or the off-board occupant sensors 140. The processor 150 may further provide adjustments to the vehicle environment by way of utilizing various actuators (described in FIG. 5 below), such as changing a physical aspect of the seat by way of using seat actuators 160B, based on the detected characteristic of the occupant. For example, in circumstances where a driver A's voice is identified by the sound sensor 127 via a voice recognition technique, the processor 150 may receive the additional control signals from the onboard occupant sensors 120 and/or the off-board occupant sensors 140 to adjust a height, an inclination, or rigidity of the seat for driver A. In embodiments, information regarding the height, inclination, or rigidity of the seat suitable for driver A may be retrieved from the memory 155 based on historical data associated with driver A's profile in circumstances where driver A had operated the vehicle and made suitable adjustments of the seat in history. For another example, in circumstances where a stretching movement of an occupant is detected by the onboard occupant sensors 120 and/or the off-board occupant sensors 140, the processor 150 may cause the seat actuators 160B to alter the rigidity level of the seat (such as changing the rigidity of the seat from a hard level to a soft level) in response to the detected stretching movement of the occupant.

It should be appreciated that any one, or any combination, of the example onboard and off-board velocity control sensors 110, 140 and the example onboard and off-board occupant sensors 120,140 could be used to predict a movement of the vehicle and alter the vehicle environment based on the predicted movement. For example, the onboard or off-board velocity control sensors 110, 140 may be used when a driver (or a computing entity embedded in the self-driving vehicle) is operating a gas pedal, a brake pedal, or a throttle to predict an accelerating or decelerating movement of the vehicle (driver-driven or self-driving). Meanwhile, the onboard or off-board occupant sensors 120, 140 may additionally be used to detect characteristic of a specific occupant for predicting adjustments to the vehicle environment to be suitable for the specific occupant. In such an example, a first control signal may be generated based on the detection results of the onboard or off-board velocity control sensors 110, 140. A second control signal may be generated based on the detection results of the onboard or off-board occupant sensors 120, 140. The processor 150 illustrated in FIG. 1 may utilize the first control signal and the second control signal jointly to predict a future movement or changes in the vehicle environment of the vehicle.

More specifically, in an example where the onboard or off-board velocity control sensors 110, 140 include a sensor for a steering wheel or other steering mechanisms, the sensor may be used when a driver is operating the steering wheel to make turns. Meanwhile, the onboard or off-board occupant sensors 120, 140 including a scale coupled to the seat, a camera, a sound sensor, a chemical sensor, or other miscellaneous sensors may additionally be used to detect a characteristic of the occupant while the driver is making turns using the steering wheel. For example, a scale coupled to the seat may detect the weight of the occupant and adjust orientation level for occupant while the vehicle is making turns (such as alter the orientation level for a greater degree for a lightweight occupant while the vehicle is making turns to better hold the occupant). In such an example, a first control signal detected by the sensor for the steering wheel and a second control signal detected by the scale are jointly used to predict a future movement or adjust the vehicle environment of the vehicle.

Figure 4:
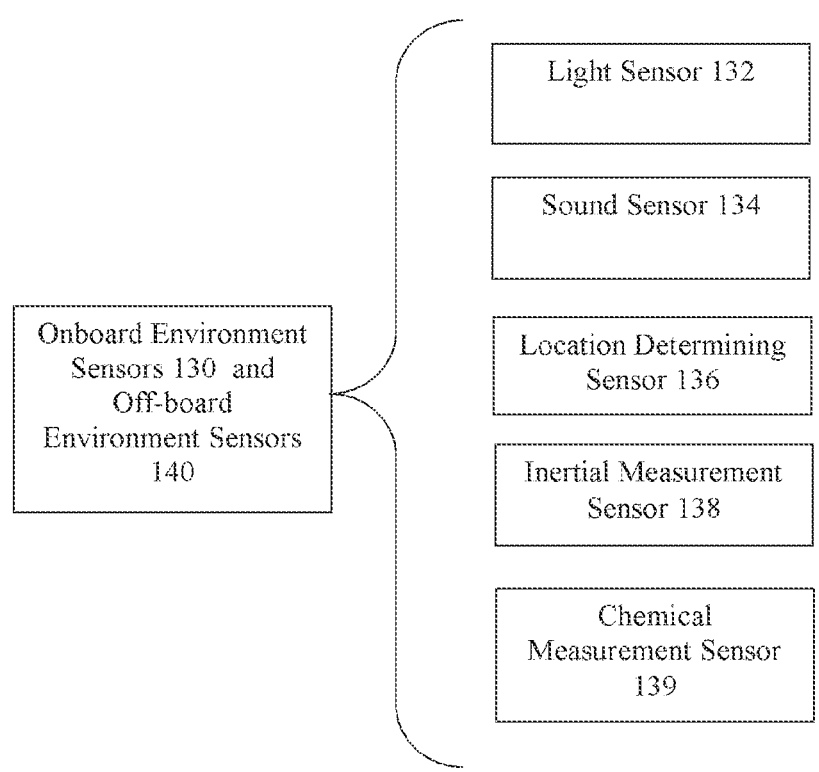
FIG. 4 is a graphic identifying various example onboard environment sensors and off-board environment sensors.

FIG. 4 is a graphic identifying various example onboard environment sensors 130 and off-board environment sensors 140.

In FIG. 4, onboard environment sensors 130 can be optionally included in the predictive control system 100 to provide yet other additional signals to the processor 150 for assisting in at least partially ameliorating an effect on an occupant based on the predicted movements. In embodiments, the onboard environment sensors 130 may include a LIDAR sensor or other light sensors 132 (such as a visible light sensor, an infrared sensor, an ultraviolet sensor, a laser sensor, etc.), an ultrasound sensor or other sound sensors 134, a GPS receiver or other location determining sensors 136, an inertial measurement sensor 138, chemical measurement sensors 139 (such as a moisture sensor), ambient weather sensors (such as wind speed sensor, wind direction sensor, ambient temperature sensor, thermometers, etc.), distance or proximity sensors, vision sensors, and/or image detecting sensors (such as cameras).

It should be appreciated that any one, or any combination, of the example onboard and off-board velocity control sensors 110, 140 and the example onboard and off-board environment sensors 130, 140 could be used to predict a movement of the vehicle and alter the vehicle environment based on the predicted movement. For example, the onboard or off-board velocity control sensors 110, 140 may be used when a driver (or a computing entity embedded in the self-driving vehicle) is operating a gas pedal, a brake pedal, or a throttle to predict an accelerating or decelerating movement of the vehicle (driver-driven or self-driving). Meanwhile, the onboard or off-board environment sensors 130, 140 may additionally be used to detect upcoming road conditions, weather conditions, and/or other ambient environment conditions for predicting potential changes to the vehicle environment. For example, in circumstances where a cavity, a bump, or an uneven payment is predicted in the upcoming road conditions based on signals received from an image sensor, a light sensor, a sound sensor, etc., the signals may separately and/or jointly be used with the vehicle control signals to determine a future movement of the vehicle. Specifically, when a cavity or a bump is detected, a vibration movement is likely to occur. For another example, in circumstances where a rainy, foggy, or snowy weather condition is detected based on signals received from the onboard or off-board environment sensors (e.g., moisture sensors, thermometers, wind speed sensors, etc.), the signals may separately and/or jointly with the vehicle control signals to determine a future movement of the vehicle. Specifically, when a rainy, foggy, or snowy weather is detected, a deceleration movement may be predicted because the driver is likely to drive slower than normal due to the slippery road condition and poor visibility for driving. In various embodiments, a first control signal may be generated based on the detection results of the onboard or off-board velocity control sensors 110, 140. A second control signal may be generated based on the detection results of the onboard or off-board environment sensors 130, 140. The processor 150 illustrated in FIG. 1, may utilize the first control signal and the second control signal independently or jointly to predict a future movement of the vehicle.

More specifically, in an example where the onboard or off-board velocity control sensors 110, 140 include a sensor for a steering wheel or other steering mechanisms, the sensor may be used when a driver is operating the steering wheel to make turns. Meanwhile, the onboard or off-board environment sensors 130, 140 including a light sensor, a sound sensor, or any other distance/proximity sensor may additionally be used to detect a distance or proximity between the vehicle and an upcoming obstruction (e.g., another vehicle in front of the vehicle the driver is occupying) while the driver is making turns using the steering wheel. In such an example, a first control signal detected by the sensor for the steering wheel and a second control signal detected by the distance or proximity sensor are independently or jointly used to predict a future movement of the vehicle.

In various embodiments, a LIDAR implementation of a light sensor 132 could be used to predict that a crash is imminent. An ordinary visual camera could detect an upcoming rough road condition, upcoming wet pavement, etc. A sound sensor 134 could detect the voice of an occupant or other person instructing "slow down," "quick, get to the hospital" or perhaps screaming A GPS or other location determining sensor 136 could be used to predict an upcoming curve in the road or track, a speed bump, gravel or other adverse road conditions. An inertial measurement sensor 138 could detect slipping, as on a wet or snowy road. A chemical measurement sensor 139 could be used to detect fog or dust in the air about the vehicle, or a smell indicative of fear of an occupant. Any of these sensors could be used to trigger a rapid deceleration, or perhaps rapid turning of the vehicle, and trigger a corresponding accommodation to the seat or other vehicle environment of the occupant, to at least partially ameliorate an effect of the predicted future movement on the occupant.

As used herein, the term "prediction" means an algorithmically produced identification of an event that is calculated to have at least a threshold likelihood of occurring within the next few seconds or minutes. In different embodiments, the prediction is for something that might occur within a time-to-event of no more than 5 seconds, 10 seconds, 30 seconds, one minute or five minutes. The time-to-event could also vary according to the severity of the predicted event. Where predictions are associated with calculated likelihoods, the threshold for acting on a prediction could have a likelihood anywhere from at least 5% to 100%, including for example at least a likelihood of 10%, 25%, 50%, 75%, and 90%, and the threshold could vary according to the severity of the predicted event.

Information used to predict velocity changes can also be obtained from onboard or off-board data stores. For example, the step of predicting a vehicle movement can comprise predicting a change in upcoming traffic based on data showing previous traffic patterns, time of the day (e.g., rush hour), day of the week (e.g., work day, or weekend) or seasons of the year (e.g., holiday), traffic reports, traffic radio, satellite data, etc. Predictions of a vehicle movement could also comprise predicting a change in ambient weather using national or regional weather data. Weather conditions contemplated to be especially relevant are occurrences of rain, snow, hail, and fog.

Predicted movements can include any movement of the vehicle 105, whether voluntary or involuntary, including acceleration and deceleration, bumps, turns, and vibrations, etc. The effects of movement of the vehicle 105 on the occupant can range anywhere from minor annoyance to motion sickness, or other severe physiological or psychological discomfort.

Information obtained from the sensors can be delivered to the processor using signals delivered in any suitable manner. The delivery of the signals may include, for example, communications using electronically, optically or mechanically, and by hard wire, wireless or optical connections.

Processor 150 is any hardware with computing ability that executes a program or algorithms Example processor 150 includes a digital/deep neuronal network (DNN) or other machine learning systems. In embodiments, processor 150 is configured to use one or more signals derived from any of the sensors 110, 120, 130, 140, as well as onboard memory/database 155 or off-board memories/databases, to predict a future movement of the vehicle 105. Processor 150 is preferably programmed such that if an inconsistent second signal is received simultaneously, or within a few seconds after receiving a first signal, the prediction of the future movement is accomplished by ignoring the first or the second signal, averaging or, in some other manner, combining the first and second signals by way of using signal mixing or blending methods (such as a sensor fusion process). Such outcomes can be based at least in part on machine learning models, for example, by training a DNN with sample data of control signals, and evaluating corresponding movements of the vehicle 105.

As illustrated in FIG. 1, processor 150 is configured to provide actuation signals to various actuators (such as vehicle actuators 160A, seat actuators 160B, or environment actuators 160C) to ameliorate effects on an occupant caused by predicted movements of a vehicle. An actuator can be any device, machinery, or equipment that may change the vehicle environment for improving occupant's onboard experience. In embodiments, the actuating signals may include signals provided to alter or adjust a component of the seat. For example, the actuation signals may be used to adjust the orientation, inclination, spatial position, distance, dimension, tension, or rigidity the seat by changing a component of the seat, including a support, a cushion, a back support, a head support, a lumbar support, a seat restraint (e.g., a seat belt), or an arm rest, etc.

For example, in circumstances where an acceleration movement of the vehicle is predicted by the processor 150 due to the operations of the acceleration pedal or an upcoming downward slope of the road condition detected by the sensors, the processor 150 may generate an actuation signal to adjust the inclination of the seat enabling the seat to incline forward to compensate the predicted acceleration movement of the vehicle. Similarly, in circumstances where a deceleration movement of the vehicle is predicted by the processor 150 due to the operations of the brake pedal or an upcoming upward slope of the road condition detected by the sensors, the processor 150 may generate an actuation signal to adjust the inclination of the seat enabling the seat to incline backward to compensate the predicted deceleration movement of the vehicle.

For another example, in circumstances where a right turn movement of the vehicle is predicted by the processor 150 due to the operations of the steering wheel or an upcoming right curve detected by the sensors, the processor 150 may generate an actuation signal to adjust the orientation of the seat enabling the seat to turn left to compensate the predicted right turn movement of the vehicle. Similarly, in circumstances where a left turn movement of the vehicle is predicted by the processor 150 due to the operations of the steering wheel or an upcoming left curve detected by the sensors, the processor 150 may generate an actuation signal to adjust the orientation of the seat enabling the seat to turn right to compensate the predicted left turn movement of the vehicle.

Figure 5:
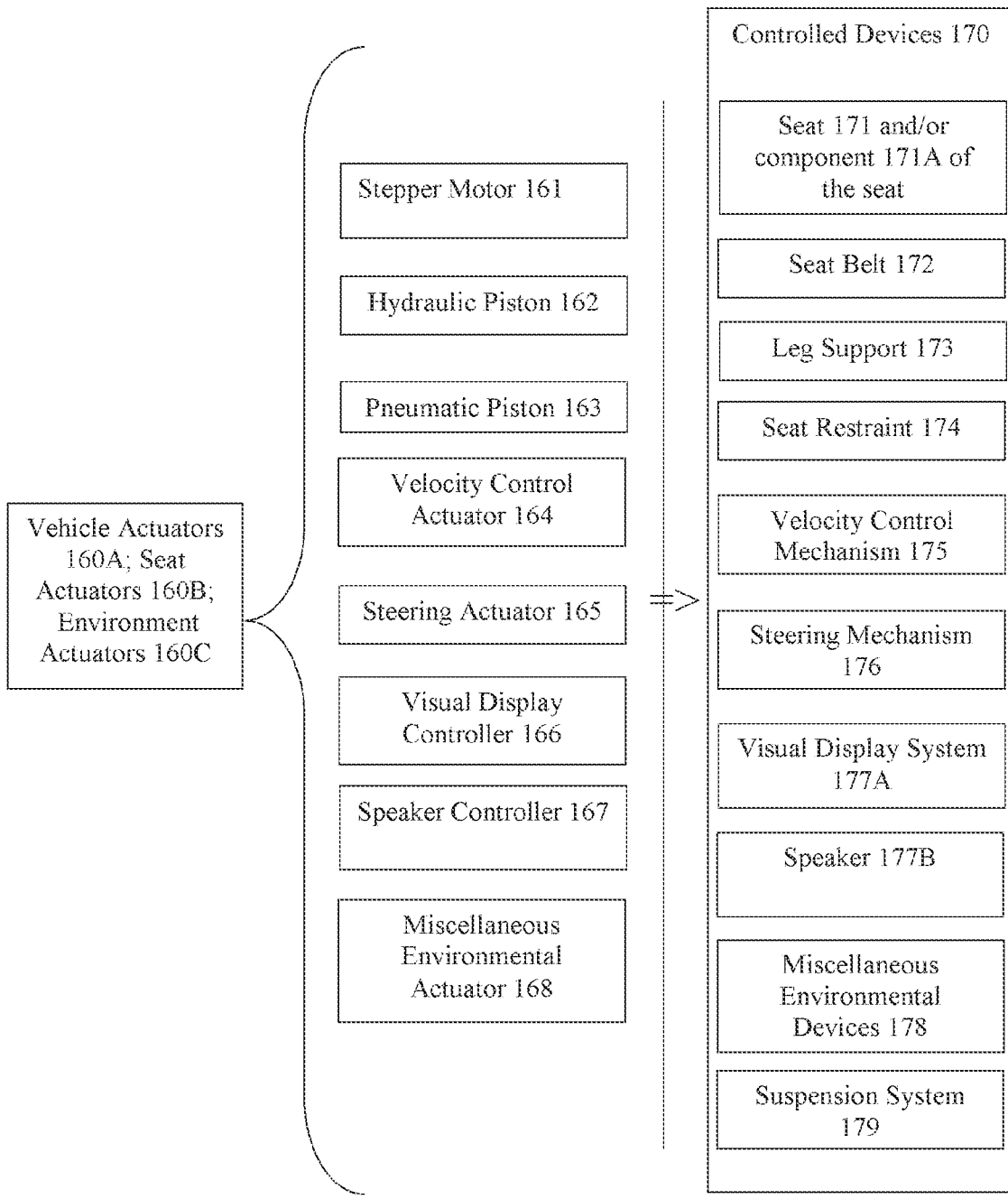
FIG. 5 is a graphic identifying various example vehicle actuators, seat actuators, and environment actuators.

FIG. 5 is a graphic identifying various example vehicle actuators, seat actuators, and environment actuators.

As shown in FIG. 5, example actuators include: vehicle actuators 160A, seat actuators 160B and environment actuators 160C, and any of these actuators that can be mechanical or non-mechanical. Example mechanical actuators include a stepper motor 161, a hydraulic piston 162, and a pneumatic piston 163. Other example actuators, which might or might not be mechanical, include a velocity control actuator 164, a steering actuator 165, a visual display controller 166, a speaker controller 167, and other miscellaneous environmental actuators 168.

Any of these actuators can be used to control one or more corresponding controlled devices 170, including a physical aspect of a seat 171 and/or a seat component 171A of the seat, a seat belt 172, a leg support 173, a seat belt or other seat restraint 174, a pedal, throttle or other velocity control mechanisms 175, a steering wheel or other steering mechanisms 176, a visual display system 177A, and a speaker 177B. Contemplated miscellaneous environmental devices 178 that can be actuated include an air conditioning or a seat temperature control device, and actuators to operate a window, a curtain, and a mirror. A suspension system 179 of the vehicle can also be actuated, for example, by altering a vehicle height, altering motion engaging or disengaging a 4WD or other anti-slip mechanisms.

Actuation signals from the processor 150 to the various actuators 160A, 160B, 160C can be delivered in any suitable manner. This includes, for example, electronically, optically or mechanically delivered signals. Electronic signals can be delivered through any combination of hard wire, wireless or optical connections.

Figure 6:
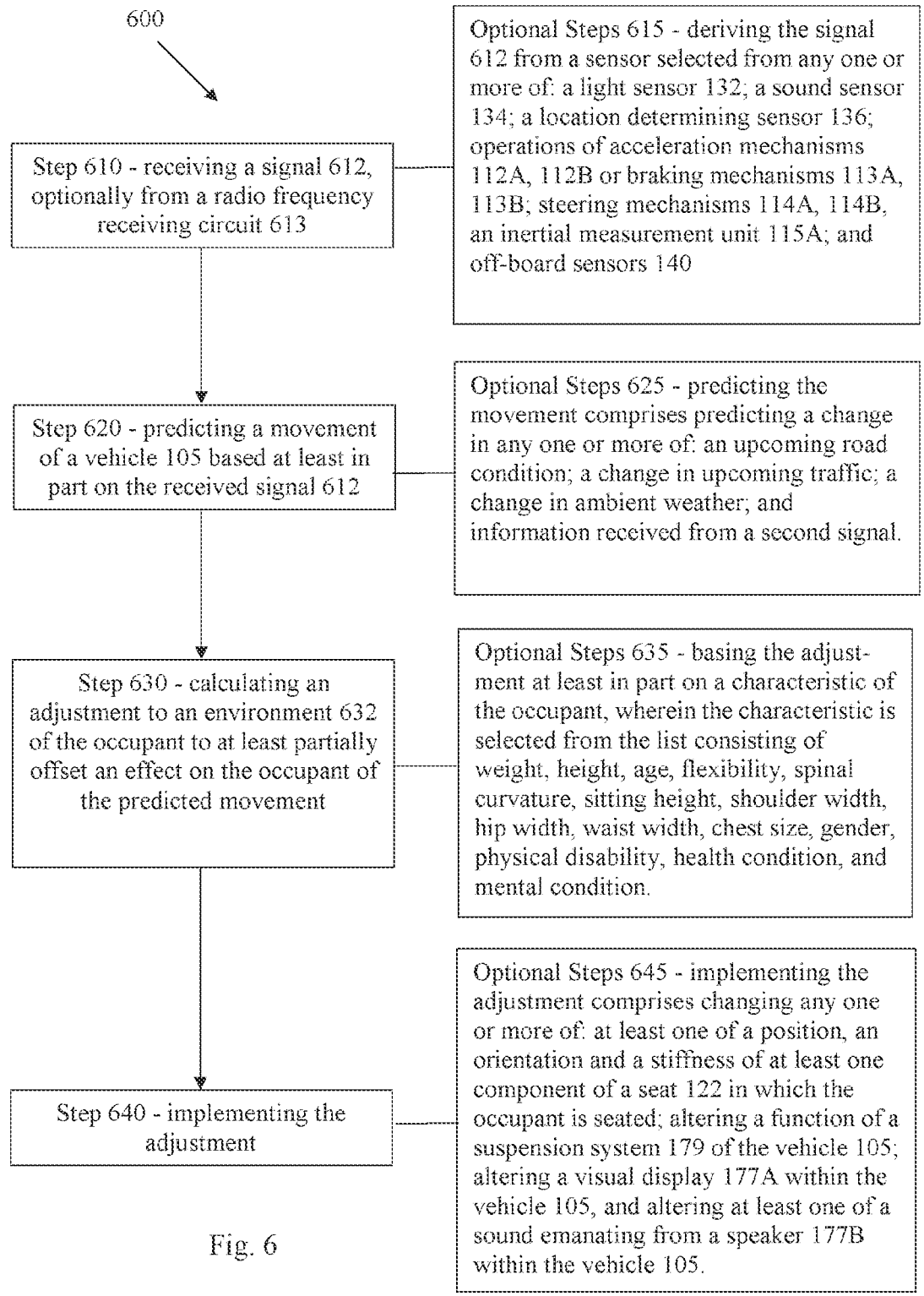
FIG. 6 is a flowchart depicting example steps of a method implementing an embodiment of the present disclosure.

FIG. 6 is a flowchart depicting example steps of a method 600 implementing an embodiment of the present disclosure.

According to an embodiment of the present disclosure, method 600 includes at least four main steps:

Step 610—receiving a signal 612, optionally from a radio frequency receiving circuit 613;

Step 620—predicting a movement of a vehicle 105 based at least in part on the received signal 612;

Step 630—calculating an adjustment to a vehicle environment 632 of the occupant to at least partially offset or compensate an effect on the occupant based on the predicted movement; and Step 640—implementing the adjustment to the vehicle environment 632.

At step 610, the signal 612 may include control signals received from onboard velocity control sensors 110, onboard occupant sensors 120, onboard environment sensors 130, or corresponding off-board sensors 140. The signal 612 may be received from a radio frequency receiving circuit 613 that is embedded on those sensors.

At step 620, the movement of the vehicle is predicted based on the received signal 612. In embodiments, the signal 612 may include control signals received from one or more onboard sensors or off-board sensors. The signal 612 may be generated by a single control signal or multiple control signals. In circumstances where multiple control signals are received, the processor 150 may generate the signal 612 by ignoring some of the control signals, averaging the multiple control signals, or combining the multiple control signals by applying different weighting parameters to each control signal. In embodiments, different weighting parameters may be pre-defined based on historical data for providing better vehicle environment to the occupant.

At step 630, after the future movement of the vehicle is predicted, a corresponding adjustment to the vehicle environment 632 of the occupant may be calculated or determined. The corresponding adjustment to the vehicle environment is calculated or determined to offset or compensate the predicted movement in advance. Due to the proactive or predictive nature disclosed in the present disclosure, the reactive and responding time to upcoming changes to the vehicle environment may be significantly reduced to offset the potential adverse effects detected and to provide a better vehicle onboard experience to the occupant.

At step 640, the calculated or determined adjustments in response to the predicted future movement may be implemented on the vehicle to alter the vehicle environment. In embodiments, the adjustments made be implemented by way of transmitting actuating signals to trigger various actuators (such as the vehicle actuators 160A, the seat actuators 160B, or the environment actuators 160C) to alter the vehicle environment. The alteration of the vehicle environment may be conducted by way of adjusting controlled devices, including one or more components of the seat, the speakers, and/or other miscellaneous environmental devices, etc.

The method 600 may optionally include sub-steps 615, 625, 635, and 645.

Optional Steps 615 include: deriving the signal 612 illustrated at step 610 from a sensor selected from any one or more of: a light sensor 132; a sound sensor 134; a location determining sensor 136; operation of an acceleration pedal 112A or other acceleration mechanisms 112B; a brake pedal 113A or other braking mechanisms 113B; a steering wheel 114A or other steering mechanisms 114B; an inertial measurement unit 115A; or off-board sensors 140.

Optional Steps 625 include: predicting the movement comprising predicting a change in any one or more of: an upcoming road condition; a change in upcoming traffic; a change in ambient weather; or information received from an additional signal.

Optional Steps 635 include: calculating the adjustment based at least in part on a characteristic of the occupant, wherein the characteristic is selected from any one or more of: a weight, a height, an age, a body temperature, a flexibility, a spinal curvature, a sitting height, a shoulder width, a hip width, a waist width, a chest size, a gender, a physical disability, a health condition, or a mental condition of the occupant.

Optional Steps 645 include implementing the adjustment comprises changing any one or more of: a position, an orientation or a stiffness of at least one component of a seat 122 in which the occupant is seated; altering a function of a suspension system 179 of the vehicle 105; altering a visual display 177A within the vehicle 105, and altering at least one of a sound or volume emanating from a speaker 177B within the vehicle 105.

Figure 7:
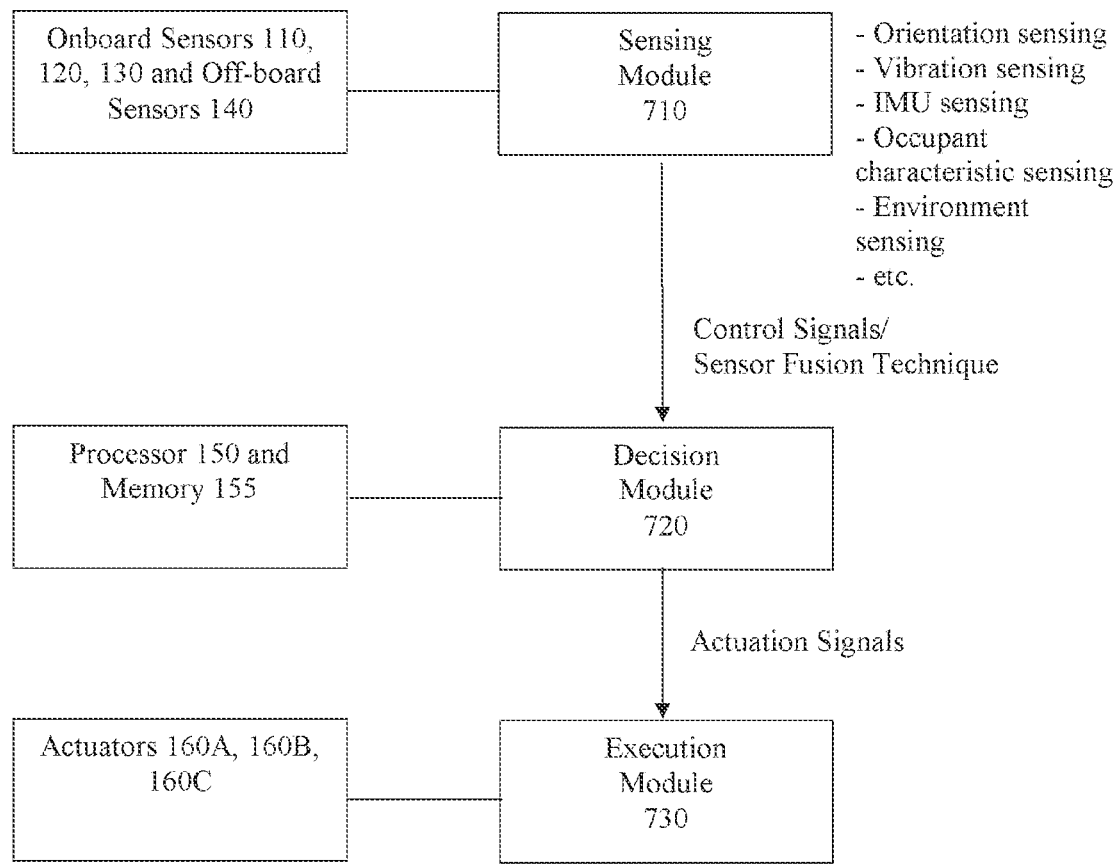
FIG. 7 is an example schematic of a predictive control system of a vehicle comprising various modules configured to alter a vehicle environment based on predicting movements of the vehicle.

FIG. 7 is an example schematic of a predictive control system of a vehicle comprising various modules configured to alter a vehicle environment based on predicting movements of the vehicle.

As illustrated in FIG. 7, the predictive control system may include a sensing module 710, a decision module 720, or an executing module 730. In embodiments of the present disclosure, the sensing module 710 may be associated with various onboard sensors (e.g., onboard velocity control sensors 110, occupant sensors 120, environment sensors 130) and off-board sensors (e.g., off-board sensors 140) for providing control signals or combined/mixed control signals by way of using sensor fusion techniques to blend information detected from different sources of sensors. The sensing module may be coupled to various sensors (as illustrated above) that perform different kinds of sensing mechanisms, including orientation sensing, vibration sensing, IMU sensing, occupant characteristic sensing, or environment sensing, etc., to provide more information to the decision module 720 for generating a more accurate prediction result of the future movements of the vehicle.

In embodiments of the present disclosure, the decision module 720 may be associated with the processor 150 and the memory 155 for determining and generating actuation signals based on a prediction result determined based on the received control signals. The generated actuation signal is determined and to be transmitted to the execution module 730 to trigger alteration to a vehicle environment to offset/compensate the predicted future movements of vehicle. For example, when an acceleration movement is predicted based on the received control signals, the decision module 720 may determine to change the inclination of the seat to lean forward. Similarly, when a deceleration movement is predicted based on the received control signals, the decision module 720 may determine to change the inclination of the seat to lean backward. For another example, when a right/left turn movement is predicted based on the received control signals, the decision module may determine to turn the seat to the left/right to offset/compensate the predicted right/left turn movement. For another example, when a vibration movement is predicted based on the received control signals, the decision module 720 may determine to change the seat in any one axis of the 3D dimensions (e.g., in pitch, roll, or yaw axis of the 3D dimensions) to offset/compensate a predicted vibration movement. In embodiments, the decision module may further make determinations based on historical control signals stored in the memory 155. The currently detected control signals received from the sensing module and previous detected historical control signals stored in the memory may independently and jointly be used to generate the actuation signals for determining an alteration/adjustment of the vehicle environment.

In embodiments, the decision module 720 can be configured to select a suitable compensation strategy from a plurality of compensation strategies based on the prediction resulting from the sensing module 710. The plurality of compensation strategies may comprise a vibration-based strategy, an inertia-based strategy, and the like. The vibration-based strategy may entail a set of pre-defined vibration-based rules for a detected vibration movement (e.g., vibration movement, oscillation movement, jerky movement) sensed by the IMU, such as lowering the height of the seat when the vehicle is likely to be lifted to a higher position due to the detection of an upcoming bump, or increasing the height of the seat when the vehicle is likely to be dropped to a lower position due to the detection of an upcoming cavity, or changing the orientation/attitude of the seat in 3D dynamics (changing orientation of the seat in any one of the pitch-axis, row-axis, and yaw-axis, or a combination thereof) about its center of gravity that is inverse to the predicted orientation/attitude, etc. The inertia-based strategy may entail a set of pre-defined inertia-based rules for a detected inertial movement (e.g., acceleration movement, deceleration movement, turning movement), such as adjusting the seat's inclination angle to tilt backward when an acceleration movement is predicted, or adjusting the seat's inclination angle to tilt forward when a deceleration movement is predicted, rotating the seat to the right with a certain rotation angle and/or tilting the seat to the right for a certain tilting angle when a left turn movement is predicted, rotating the seat to the left with a certain rotation angle and/or tilting the seat to the left for a certain tilting angle when a right turn movement is predicted, etc.

The suitable compensation strategy may be selected, based on the characteristics (e.g., vibration-based or inertia-based) of the prediction result, from one or more of the corresponding vibration-based strategy, the inertia-based strategy, etc. The suitable compensation strategy may also be selected based on a combination of multiple compensation strategies in circumstances where the predicted result has multiple characteristics. For example, when upcoming bumps on an upward slope road section is detected, a vibration-based movement due to the bumps and an inertia-based movement due to the upward slope road section may be detected simultaneously by the sensing module 710 based on different sensors. In such an example, the decision module 720 may determine a suitable compensation strategy that encompasses a combination or an aggregation of the vibration-based strategy and the inertia-based strategy, such as a suitable compensation strategy encompassing a subset of rules included in the vibration-based strategy and a subset of rules included in the inertia-based strategy. The selection of the suitable compensation strategy may be based on other characteristics, including the characteristics of the prediction results (e.g., the type of predicted movement, the magnitude of predicted movement, etc.), the characteristics of the vehicle, the characteristics of the occupant (occupant's preferences, occupant's weight, sitting height, arm length, etc.), and/or the like. Specifically, in circumstances where a prediction result of a predicted vibration-based movement is sensed by the IMU, the decision module 720 may further determine a suitable compensation strategy considering the occupant's preferred sitting height. For example, in circumstances where the vehicle is predicted to be dropped to a lower position due to the detection of an upcoming cavity, decision module 720 may further determine a specific height adjustment based on the preferred sitting height of a specific occupant (such as increasing the seat height with a larger degree when the sitting height of an occupant is preferred to be higher than a default threshold, increasing the seat height with a smaller degree when the sitting height of another occupant is preferred to be lower than the default threshold, etc.).

As illustrated in FIG. 7, compensation strategies can have corresponding execution mechanisms conducted by the execution module 730 via actuation signals received form the decision modules 720, where the actuation signals may be generated based on a suitable compensation strategy selected by the decision module 720. Once a suitable compensation strategy is selected from a plurality of compensation strategies based on the prediction resulting from the sensing module 710, the execution module 730 may conduct corresponding execution mechanisms in compliances with the rules associated with the suitable compensation strategy.

Specifically, in circumstances where the vibration-based compensation strategy is determined based on a detected vibration movement (e.g., vibration movement, oscillation movement, jerky movement) sensed by the IMU, corresponding vibration-based execution mechanisms are conducted by the execution module 730 to offset/compensate the detected vibration movement. For example, if a vibration-based rule of lowering the height of the seat is selected when the vehicle is likely to be lifted to a higher position due to the detection of an upcoming bump, the execution module 730 may conduct a corresponding vibration-based execution mechanism to lower the seat height. For another example, if a vibration-based rule of increasing the height of the seat is selected when the vehicle is likely to be dropped to a lower position due to the detection of an upcoming cavity, the execution module 730 may conduct a corresponding vibration-based execution mechanism to increase the seat height. For another example, if a vibration-based rule of changing the orientation/attitude of the seat in 3D dynamics is detected, the execution module 730 may conduct a corresponding vibration-based execution mechanism to alter the orientation/attitude of the seat in 3D dynamics inversely (changing orientation in any one of the pitch-axis, row-axis, and yaw-axis, or a combination thereof to be inverse to the predicted future orientation/attitude changes) to offset/compensate the detected vibration-based orientation/attitude movement.

Specifically, in circumstances where the inertia-based compensation strategy is determined based on a detected inertial movement (e.g., acceleration movement, deceleration movement, turning movement), corresponding inertia-based execution mechanisms are conducted by the execution module 730 to offset/compensate the detected inertial movement. For example, if an inertia-based rule of adjusting the seat's inclination angle to tilt backward is selected when an acceleration movement is predicted, the execution module 730 may conduct a corresponding inertia-based execution mechanism to alter the seat's components (e.g., a seat back support, a seat bottom part, etc.) such that the seat can be tilted backward. For another example, if an inertia-based rule of adjusting the seat's inclination angle to tilt forward is selected when a deceleration movement is predicted, corresponding inertia-based execution mechanisms are conducted by the execution module 730 to alter the seat's components (e.g., a seat back support, a seat bottom part, etc.) such that the seat can be tilted forward. For another example, if an inertia-based rule of rotating the seat to the right/left with a certain rotation angle and/or tilting the seat to the right/left for a certain tilting angle is selected when a left/right turn movement is predicted, corresponding inertia-based execution mechanism are conducted by the execution module 730 to alter the seat such that the seat can be rotated to the right/left with a certain rotation angle and/or tilting to the right/left with a certain tilting angle.

In embodiments, when the suitable compensation strategy is selected from one or more of the vibration-based compensation strategy, the inertia-based strategy, and/or other compensation strategies, the corresponding execution mechanisms may be conducted jointly based on the selection. The corresponding execution mechanisms are conducted jointly such that combined or aggregated adjustments of the vehicle environment that are based on different detected characteristics (e.g., vibration-based or inertia-based) of the predicted adverse movement may take into effects simultaneously for providing better compensation movements to eliminate the predicted adverse movement. In embodiments, the selection of the suitable compensation strategy may further be based on other characteristics, including the characteristics of the prediction results (e.g., the type of predicted movement, the magnitude of predicted movement, etc.), the characteristics of the vehicle, the characteristics of the occupant (occupant's preferences, occupant's weight, sitting height, arm length, etc.), and/or the like. In such embodiments, corresponding execution mechanisms that are associated with these additional characteristics, including the characteristic of the prediction results, the vehicle, the occupant, and/or the like, may further be considered to better eliminate the predicted adverse movement. Specifically, additional execution mechanisms may be conducted by the execution module 730 for a specific prediction result (e.g., considering the degree of turning angle for a turning movement, the steepness of the road condition for an upcoming upward/downward slope road section, the degree of vibration magnitude for a vibration movement, etc.), for a specific vehicle (e.g., considering a lower chassis of a sport car comparing to a regular car, a higher chassis of a sports utility vehicle (SUV) comparing to a regular car, etc.), and/or for a specific occupant (e.g., considering the sitting height, the weight, the arm length, the shoulder width, etc. of a specific occupant). Due to the considerations of the various characteristics, such as characteristics of the predicted future movements, the predicted results, the vehicle, and/or the occupant, the system prosed in the present disclosure may proactively adjust the vehicle environments based on multiple factors, including the predicted future movements of the vehicle, the unique features of the vehicle, and/or unique feature of the occupant, and may provide a precise adjustment and a better vehicle experience to an occupant.

In embodiments of the present disclosure, the execution module 730 may be associated with various actuators (e.g., vehicle actuators 160A, seat actuators 160B, or environment actuators 160C). The execution module 730 receives the actuation signals generated from the decision module 720 to alter or make adjustments to seat environment. Vehicle actuators 160A may include speed actuators (e.g., throttle or brake) and/or steering actuators. For example, when a deceleration or stop movement is predicted to avoid collisions to an obstruction or previous vehicle, the vehicle actuators 160A may be triggered by the execution module to lock the acceleration pedal or trigger the brake pedal to stop the vehicle or turn the vehicle around the obstruction. For another example, when an orientation, inclination, rigidity of the seat is determined to be altered, the execution modules may trigger the seat actuator 160B to adjust one or more components of the seat. For another example, when a deceleration or stop movement is detected to stop the vehicle, the execution module 730 may turn on the volume of the speaker and provide audio warnings to alert the driver or passenger of the predicted adverse road condition or possible collisions.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims at least one of something selected from the group consisting of A, B, C . . . and N, the text should be interpreted as requiring only one element from the group, not A plus N, or B plus N, etc.

What is claimed is:

1. An active seat control system for use in a vehicle having a seat, comprising:
   a velocity control sensor configured to derive a first control signal;
   an occupant sensor configured to provide a second control signal based on detecting a characteristic of an occupant held by the seat;
   an actuator coupled to the seat, the actuator comprising a velocity control structure; and
   a processor configured to:
      predict a future movement of the vehicle based on the first control signal,
      generate an actuation signal based on the predicted future movement of the vehicle and the second control signal,
      and
      provide the actuation signal to the actuator before actual movement of the vehicle corresponding to the future movement of the vehicle to cause the actuator to operate the velocity control structure to at least partially ameliorate an effect that would likely occur due to the predicted future movement.

2. The system of claim 1, wherein the velocity control sensor is configured to detect operations of an acceleration pedal or a braking pedal.

3. The system of claim 1, wherein the velocity control sensor is configured to detect operations of a steering wheel.

4. The system of claim 1, wherein the actuator comprises one or more of a stepper motor, a hydraulic piston or a pneumatic piston.

5. The system of claim 1, further comprising a memory, wherein the processor is further configured to produce the actuation signal based at least on historical data stored in the memory.

6. The system of claim 1, wherein the characteristic of the occupant is associated with one or more of a weight, a height, a flexibility, a body temperature, a spinal curvature, a sitting height, a shoulder width, a hip width, a waist width, a chest size, an age, a gender, a physical disability, a health condition, or a mental condition of the occupant.

7. The system of claim 1, wherein the actuator controls at least one of a distance, an orientation, a spatial position, a tension, or a rigidity of at least one component of the seat.

8. A method for controlling a vehicle environment of a vehicle, comprising:
   receiving a first signal;
   predicting a movement of the vehicle based at least on the received first signal;
   determining an adjustment to the vehicle environment based at least on a characteristic of an occupant and the predicted movement of the vehicle to at least partially ameliorate an effect on the vehicle that would likely occur due to the predicted movement; and
   implementing the adjustment to the vehicle environment before actual movement of the vehicle corresponding to the predicted movement of the vehicle.

9. The method of claim 8, further comprising deriving the first signal from at least one sensor comprising one or more of a location determining sensor, a light sensor, or a sound sensor.

10. The method of claim 8, further comprising deriving the first signal from at least one of a sensor for a braking mechanism or an inertial measurement unit.

11. The method of claim 8, wherein the first signal is received from an off-board velocity control sensor.

12. The method of claim 8, wherein predicting the movement of the vehicle comprises predicting a change in at least one of an upcoming road condition, upcoming traffic, or ambient weather.

13. The method of claim 8, wherein predicting the movement of the vehicle is further based on a second signal.

14. The method of claim 8, wherein the characteristic of the occupant is associated with one or more of a weight, a height, an age, a flexibility, a body temperature, a spinal curvature, a sitting height, a shoulder width, a hip width, a waist width, a chest size, a gender, a physical disability, a health condition, or a mental condition of the occupant.

15. The method of claim 8, wherein implementing the adjustment to the vehicle environment comprises changing at least one of a stiffness, a function, a position or an orientation of at least one component of a seat in which an occupant is seated.

16. The method of claim 8, wherein implementing the adjustment to the vehicle environment comprises altering at least one of a digital object rendered on a visual display within the vehicle or a volume or content of acoustic signals emanating from a speaker within the vehicle.

17. A vehicle having a seat and an active seat control system, comprising:
   an actuator coupled to the seat; and
   a processor configured to:
      receive an electronic signal,
      predict a future movement of the vehicle based on the electronic signal,
      generate an actuation signal based on the predicted future movement of the vehicle and a second control signal based on detecting a characteristic of the occupant, and
      provide an actuation signal to the actuator before actual movement of the vehicle corresponding to the future movement of the vehicle to cause the actuator to at least partially ameliorate an effect that would likely occur due to the predicted future movement of the vehicle by altering one or more of a distance or an orientation of a component of the seat.

18. The vehicle of claim 17, further comprising a sensor configured to produce the electronic signal, wherein the sensor comprises one or more of a pressure sensor, a motion sensor, a LIDAR sensor, a light sensor, a location sensor, a sound sensor, or a location determining sensor.

19. The vehicle of claim 17, wherein the vehicle is a self-driving vehicle.

20. The vehicle of claim 17, wherein the vehicle is a public transportation vehicle.

\* \* \* \* \*